(12) United States Patent
Nisato et al.

(10) Patent No.: US 8,048,019 B2
(45) Date of Patent: Nov. 1, 2011

(54) MULTIPLE NOZZLE TRANSDERMAL DRUG DELIVERY SYSTEM

(75) Inventors: Giovanni Nisato, Eindhoven (NL); Jean-Christophe Baret, Göttingen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/442,958

(22) PCT Filed: Sep. 26, 2007

(86) PCT No.: PCT/IB2007/053917
§ 371 (c)(1),
(2), (4) Date: Feb. 10, 2010

(87) PCT Pub. No.: WO2008/038240
PCT Pub. Date: Apr. 3, 2008

(65) Prior Publication Data
US 2010/0143448 A1      Jun. 10, 2010

Related U.S. Application Data

(60) Provisional application No. 60/827,493, filed on Sep. 29, 2006.

(51) Int. Cl.
*A61B 17/20* (2006.01)
*A61M 5/30* (2006.01)

(52) U.S. Cl. ............................................. 604/22; 604/68
(58) Field of Classification Search .................. 604/22, 604/68, 71, 72, 19, 180, 191, 892.1, 890.1
See application file for complete search history.

(56) References Cited

U.S. PATENT DOCUMENTS

| | | | |
|---|---|---|---|
| 2003/0117371 A1* | 6/2003 | Roberts et al. | 345/156 |
| 2006/0184101 A1 | 8/2006 | Srinivasan et al. | |
| 2006/0216337 A1 | 9/2006 | Van Laar | |

FOREIGN PATENT DOCUMENTS

| | | |
|---|---|---|
| WO | 2004012795 A2 | 2/2004 |
| WO | 2004093818 A2 | 11/2004 |
| WO | 2006086742 A2 | 8/2006 |

* cited by examiner

*Primary Examiner* — Nicholas D Lucchesi
*Assistant Examiner* — Brooke Matney

(57) ABSTRACT

A transdermal drug delivery system (100) for providing controlled doses of a drug through the skin of a human or other animal is disclosed. In one embodiment, the transdermal drug delivery system (100) includes a substrate (110) designed to adhere to skin and a transdermal injector array (140) coupled to the substrate (110). The transdermal array (140) has one or more transdermal injectors (210, 220, 230) embedded within including a first transdermal injector (210) configured to administer or provide a first substance to the skin at a speed great enough to produce an appreciable breach in the surface of the skin.

21 Claims, 2 Drawing Sheets

MULTIPLE NOZZLE TRANSDERMAL DRUG DELIVERY SYSTEM

Broadly defined, a transdermal drug delivery system is any system designed to administer an appreciable dose of some drug directly through the skin without use of a conventional hypodermic needle. Examples of transdermal drug delivery systems include "the patch" (i.e., an adhesive patch design to deliver nicotine to tobacco-addicted people), aspirin-laced balms and adhesive patches designed to administer highly potent pain-killers.

While the hypodermic or oral administration of a drug is often the preferred method of drug delivery, transdermal drug delivery provides a number of advantages including the release of medication over prolonged periods and favorable patient feedback.

Unfortunately, existing transdermal patches lack versatility, and their effectiveness can be hampered by the kinetics of the drug used, skin interaction and drug solubility. Further, existing transdermal patches cannot provide periodic dosing or dosing on demand. Still further, there are a wide variety of drugs that do not readily permeate human skin. Accordingly, new technology related to transdermal drug delivery systems is desirable.

A transdermal drug delivery system is disclosed for providing controlled doses of a drug through the skin of a human or other animal. The transdermal drug delivery system includes a thin adhesive substrate for adhering to skin, and at least one transdermal injection means coupled to the substrate for administering or providing a first substance to the skin to produce an appreciable breach in the surface of the skin.

The transdermal injection means may be a transdermal injector array having one or more transdermal injectors embedded within, including at least one transdermal injector configured for administering or providing at least one substance to the skin to produce an appreciable breach in the surface of the skin.

The transdermal injection means may further be a a piezoelectric-driven transdermal injector coupled to the substrate, the transdermal injector configured to administer or provide a plurality of different substances to the skin including a first substance to produce an appreciable breach in the surface of the skin.

Based on one or more of the above illustrative embodiments, the various advantages offered by the disclosed methods and systems include providing a "drug on demand" system where, as opposed to conventional transdermal patches, the doses delivered can be made according to any number of timed intervals. Further, both individual doses and total dosage can be adjusted on the fly and from one patient to another taking into account different body weights or metabolisms.

The following detailed description is best understood when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

In the following detailed description, for purposes of explanation and not limitation, specific details of exemplary embodiments are set forth in order to provide a thorough understanding of the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatus and methods may be omitted so as to not obscure the description of the exemplary embodiments. Such methods and apparatus are clearly within the scope of the present teachings.

Figure 1:
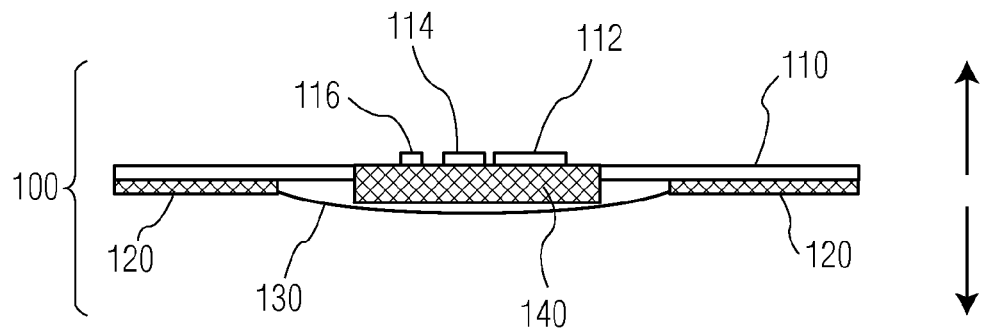
FIG. 1 shows a cross-sectional side view of an exemplary transdermal drug delivery system according to the disclosed methods and systems.

FIG. 1 shows an exemplary transdermal drug delivery system 100. As shown in FIG. 1, the exemplary transdermal drug delivery system 100 includes a flexible substrate 110 having a user interface 116, a controller 114 and a battery 112 disposed (directly or indirectly) upon the upper side of the substrate 110. An adhesive 120 is disposed upon the lower side of the substrate 110 to secure the substrate 110 to a patient's skin. A transdermal injector array 140 is embedded within the substrate 110, and an optional anti-bacterial gel 130 can be disposed upon the transdermal injector array 140.

Figure 2A:
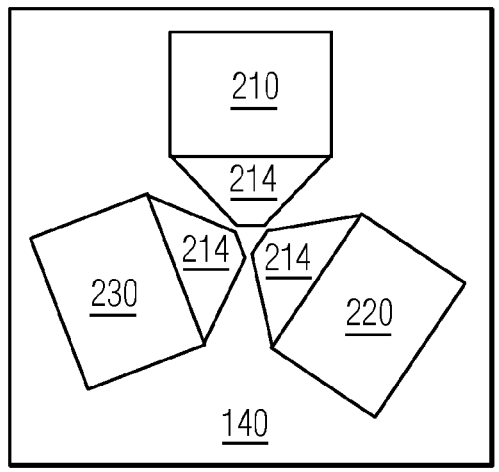
FIG. 2A shows a top-down view of an exemplary transdermal injector array.

FIG. 2A shows a top-down view of the transdermal injector array 140 of FIG. 1. The transdermal injector array 140 includes three transdermal injectors 210, 220 and 230 with each transdermal injector 210, 220 and 230 having a respective nozzle 214 and each of the three nozzles 214 being placed in close proximity to one another.

The transdermal injectors 210, 220 and 230 can operate in concert for the same purpose or independently of one another and with different purposes from one another. For example, the first transdermal injector 210 can be used to cause a breach in the outermost skin surface layer (stratum corneum); the second transdermal injector 220 then can be used to administer or provide various drugs or other medicating agents to the skin breach; and the third transdermal injector 230 can be used to seal the skin breach as well as provide various healing agents to the skin breach. It is emphasized that the use of three transdermal injectors is merely illustrative and that more or fewer injectors may be used.

For causing a desired skin breach, the first skin-disrupting transdermal injector 210 can employ a payload of water or a water-based solution to create a jet having a jet speed in the range of about 60 to 160 meters/second. The high speed of the resultant jet is used to create the desired skin breach. A benefit of the skin breach is that various drug molecules that could never otherwise penetrate human/animal skin in an effective dose can now be administered into a patient's bloodstream via the skin breach. That is, use of the first skin-disrupting transdermal injector 210 can enable a latter-applied payload of any number of medicating agents to be effectively delivered.

Skin breaches can represent open paths for bacteria. Accordingly, once the appropriate medicating agent has been administered, the third transdermal injector 230 can deliver a "clotting" substance in order to reduce the adverse effects that may result from the breach or breaches in the stratum corneum caused by the injection process. The payload of the third transdermal injector 230 can include a polymer mixture with a gelling point of about 37° C. to plug the breach and/or a gel with relatively large adhesion on the skin which, with the aid of evaporation, can impart a mechanical stress to the skin to help close each skin breach. The payload of the third transdermal injector 230 can also include any number of anti-bacterial agents, such as a low viscosity mixture of oil, water and silver, proteins that promote tissue recovery, or any number of other agents that can aid in the healing process.

Figure 2B:
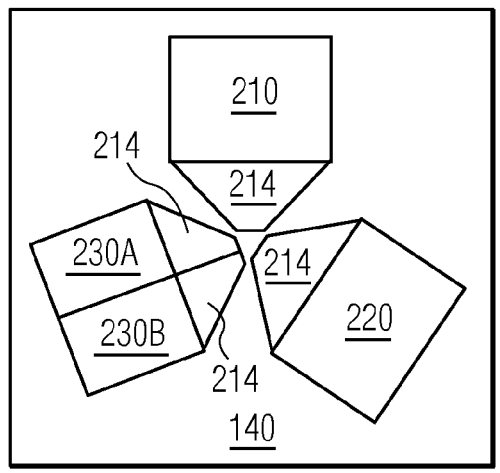
FIG. 2B shows a top-down view of an alternative embodiment to the embodiment shown in FIG. 2A.

FIG. 2B shows an alternative embodiment to FIG. 2A, in which the third transdermal injector 230 is replaced by a plurality of injectors, which is particularly suitable for in-situ chemical, biological, or biochemical reactions. That is, third transdermal injector 230 is replaced by a first transdermal injector 230A and a second transdermal injector 230B. First transdermal injector 230A dispenses a mixture of different monomers and second transdermal injector 230B dispenses a crosslinker for the polymerization of the monomers. The mixing of the monomer(s) and crosslinker can then occur on a patient's skin or within a common internal chamber before being deposited on the patient's skin.

In another alternative embodiment which is not illustrated, two different substances can be administered or provided from the same injector. For example, both a skin-breaching substance and a medicating agent can be delivered using the first transdermal injector 210. However, the second transdermal injector 220 can be designed to deliver its own medicating payload at a lower speed, typically about five meters/second or less. An advantage of using the lower jet speed is to decrease the degradation of certain medicating agents that might otherwise occur due to the transdermal injection process. For instance, shear rates occurring during the delivery of high molecular weight polypeptides (used in gene therapy or vaccination) at the jet speeds necessary to break the skin surface layer can degrade the polypeptides while jet speeds at five meters/second will have a negligible affect.

Also, one or more of the transdermal injectors 210, 220 and 230 can share a common opening at the bottom of the transdermal injector array body as well as share portions of a common nozzle.

While the transdermal injector array 140 of FIGS. 1, 2A and 2B is depicted and described as having multiple injectors with each injector serving a different function, it should be appreciated that the disclosed methods and systems can be expanded to include a system with an injector array where multiple nozzles are used to deliver simultaneous doses of one or more drugs (i.e. parallel dispensing), thus enabling a larger dynamic range for drug delivery. Additionally, using multiple nozzles can provide a more robust device, especially when one or more sensors are added to detect malfunctions (e.g. piezo element sensing pressure), which could determine when a nozzle is damaged or clogged. Malfunction information can be provided to the user interface 116 to provide a visible indication to the patient, be recorded by the controller 114 or be wirelessly communicated to some base unit such that a health care professional (nurse, medical doctor etc.) can take appropriate measures.

Figure 3:
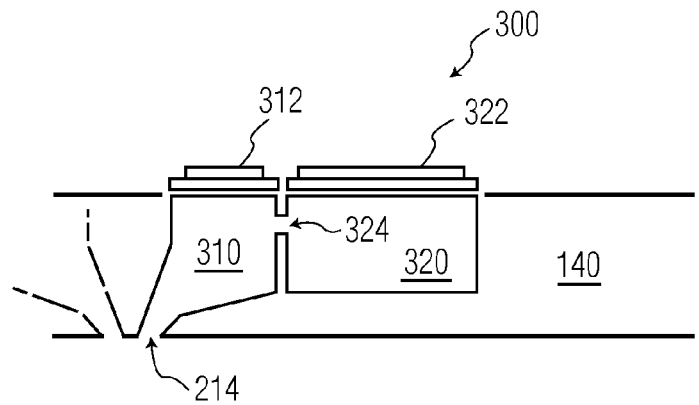
FIG. 3 shows an exemplary transdermal injector.

FIG. 3 shows another exemplary transdermal injector generally designated as transdermal injector 300. As shown in FIG. 3, the transdermal injector 300 includes a holding chamber 310 having a nozzle 214 at the bottom and a first actuator 312 (typically a piezoelectric device, but not limited thereto) lining the top of the holding chamber 310. The holding chamber 310 is coupled to a reservoir 320 via passage 324, and a second actuator 322 can line the top of the reservoir 320.

In operation, the second actuator 322 is activated to force a number of fluids from the reservoir 320 through passage 324 and into the holding chamber 310. Once the resident fluid(s) have been expelled from the holding chamber 310, the second actuator 322 is activated again to refill the holding chamber 310 for the next delivery of the transdermal injector 210.

Alternative to the embodiment in FIG. 3, if multiple substances need to be simultaneously or serially administered or provided (such as the monomer/crosslinker example above), multiple reservoir chambers (not shown) are coupled to the holding chamber 310. Once the holding chamber 310 is appropriately filled, the first actuator 312 is activated to propel fluid residing within the holding chamber 310, through the nozzle 214 to create a jet, thereby dispensing the resident fluid onto or into a patient's skin.

The particular velocity of any resultant jet can vary as a function of the first actuator's configuration. Multiple actuators may be substituted for the first actuator 312 in order to control jet speed. For example, by employing an array of three actuators, it can be possible to dispense fluids from the holding chamber 310 at as many as seven different speeds.

Where a transdermal injector employs multiple reservoir chambers, each of the one or more other reservoir chambers (not shown) can be used to fill the holding chamber 310 with a different fluid to be subsequently expelled. For example, a transdermal injector can have four separate reservoir chambers for separately holding and serially passing any one of the following to a holding chamber to be expelled: (1) a skin-breaching substance, (2) a medicating agent, (3) a polymer mixture and (4) an antiseptic.

Figure 4:
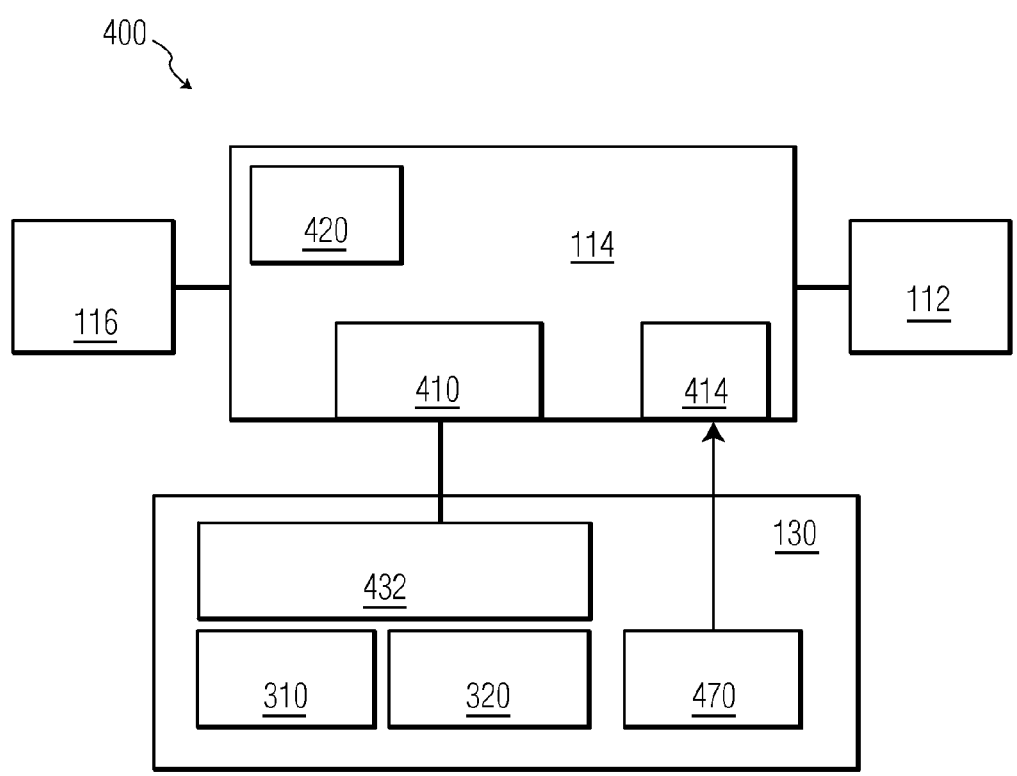
FIG. 4 is a block diagram of a transdermal drug delivery system.

Continuing to FIG. 4, a transdermal delivery system 400 is shown. Most of the elements 110-140 of FIG. 1 are shown, as well as a number of sensors 470 (contained in the gel 130 and/or in the adhesive layer 120). Various internal components of the controller 114 are also shown including a timer 420, a driver array 410, an actuator array 432, and an analog-to-digital ("ADC") converter 414 for monitoring the sensors 470.

In operation and under power provided by the battery 112, the controller 114 is initialized via the user interface 160. User interface 116 is a combination of an activation button and multicolored light-emitting diode—the button for initiating a drug administration or for starting a sequence of timed drug administrations, and the diode for indication system status, e.g., active/inactive/depleted, good/fail/fault etc. However, in other embodiments, the user interface 116 can take a large variety of forms, such as a wired or wireless computer-to-computer interface. In such instances, the transdermal system 400 can be activated and programmed to administer or provide certain medicating doses at precise intervals and/or at specific times.

Assuming that the transdermal system 400 is applied to a patient's skin with the controller 114 suitably programmed and activated, the controller 114 can carry out its basic programming, which can include appropriately setting and resetting the timer 420, appropriately activating the transdermal injector array 140 and monitoring the various sensors 470 for patient feedback.

The actuator array 432 is operable to activate one or more reservoirs 320 to pass a fluid to a holding chamber 310, and the same actuator array 432 is operable to activate the holding chamber 310 to expel the fluid therefrom.

Also during operation, the sensors 470 can be used to provide various forms of feedback, such as using skin resistance to determine whether the transdermal system 400 is appropriately attached, determining the temperature of the patient's skin, determining pulse rate and blood oxygen, monitoring for irritation and swelling and so on. Also, the administration of a particular drug can be regulated using feedback. For example, assuming that an infrared pulse-oximeter is employed to measure pulse rate, the transdermal system 400 can be used to deploy various stimulants whenever a patient's pulse drops below a certain rate.

In addition, the sensors 470 can be used to provide basic self-testing functions, such as allowing the controller to determine whether a particular injector is functioning, whether a reservoir is empty and so on.

Returning to FIG. 4, it should be appreciated that various embodiments of the above-described system 400 can have distinct advantages over any conventional drug delivery system. Highly portable and ergonomic drug-delivery systems can be manufactured that can be precisely timed to deliver precise doses. Drugs having molecular structures not subject to skin absorption can be administered in the form of a skin-patch. Further, the employment of an appropriate controller and user interface can allow a medical professional to monitor patient usage, e.g., monitor how many times a patient self-medicated himself and over what intervals.

In various embodiments where the above-described systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like.

Accordingly, various storage media, such as magnetic computer disks, optical disks, electronic memories and the like, can contain information that can direct a device, such as a computer, to implement the above-described systems and/or methods. Once an appropriate device has access to the information and programs contained on the storage media, the storage media can provide the information and programs to the device, thus enabling the device to perform the above-described systems and/or methods.

For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware and software. Further, the various methods and parameters are included by way of example only and not in any limiting sense. In view of this disclosure, those skilled in the art can implement the present teachings in determining their own techniques and needed equipment to effect these techniques, while remaining within the scope of the appended claims.

The invention claimed is:

1. A transdermal drug delivery system for providing controlled doses of a drug through skin, the transdermal drug delivery system comprising:
   a thin adhesive substrate which adheres to skin;
   a transdermal injector array coupled to the substrate, the transdermal injector array having a plurality of transdermal injectors including:
      a first transdermal injector which administers a first substance to the skin which produces an appreciable breach in the surface of the skin,
      a second transdermal injector which administers a medicating agent to the skin breach, and
      a third transdermal injector which administers a healing agent to the skin breach; and
   a controller coupled to each transdermal injector, the controller controls the first, second, and third transdermal injectors sequentially to administer the first substance to breach the skin, then the medicating agent to the skin breach, then the healing agent to the medicated skin breach, as a function of at least one of a user request and a preprogrammed timed regiment.

2. The transdermal drug delivery system of claim 1, wherein each transdermal injector includes a holding chamber with a nozzle, and wherein each holding chamber includes an actuator configured to expel a substance from the holding chamber through the nozzle and onto the skin, the second transdermal injector expelling the medicating agent at a lower velocity than the first transdermal ejector ejects the first substance.

3. The transdermal drug delivery system of claim 2, wherein the holding chamber actuator is a piezoelectric device.

4. The transdermal drug delivery system of claim 2, wherein the medicating agent includes a high molecular weight polypeptide, the second transdermal injector ejecting the medicating agent at a sufficiently low velocity that shearing of the polypeptide is avoided.

5. The transdermal drug delivery system of claim 1, wherein each transdermal injector further includes a reservoir coupled to the holding chamber and each reservoir includes a reservoir chamber actuator configured to expel a substance from the reservoir into the holding chamber.

6. The transdermal drug delivery system of claim 1, further comprising a user interface coupled to the controller.

7. The transdermal drug delivery system of claim 6, wherein the user interface includes at least one of a visual indicator and a computer-to-computer interface.

8. The transdermal drug delivery system of claim 1, wherein the transdermal array has at least two transdermal injectors that share a portion of a nozzle.

9. The transdermal drug delivery system of claim 1, wherein the third transdermal injector includes a first injector unit that ejects monomers and a second injector unit that ejects a crosslinking agent for polymerization of the monomers.

10. The transdermal drug delivery system of claim 1, wherein the healing agent includes a gel which adheres to the skin and imparts a mechanical stress to the skin that urges the skin breach to close.

11. The transdermal drug delivery system of claim 1, wherein the healing agent includes at least one of a clotting agent and an antiseptic.

12. A transdermal drug delivery method for providing controlled doses of a drug through the skin of a human or other animal, the transdermal drug delivery method comprising:
   adhering a thin adhesive substrate to which a plurality of transdermal injectors are coupled to a surface of the skin;
   administering a first substance to the skin to produce an appreciable breach in the surface of the skin with a first of the transdermal injectors; and
   after breaching the skin, administering a medicating agent to the skin breach with a second of the transdermal injectors, the medicating agent being absorbed through the skin breach.

13. The method of claim 12, further including:
   after administering the medicating agent, administering the healing agent which includes a gel which plugs the skin breach.

14. The method of claim 12, wherein the medicating agent includes a polypeptide and wherein the medicating agent administering step is performed at a velocity low enough to avoid shearing of the polypeptide.

15. The method of claim 12, further including:
   after administering the medicating agent, administering a gel which forms a film over the skin breach.

16. The method of claim 15, further including:
with the gel, imparting a mechanical stress that urges the skin breach to close.

17. A transdermal drug delivery system for providing controlled doses of a drug through the skin of a human or other animal, the transdermal drug delivery system comprising:
a thin adhesive substrate designed to adhere to skin;
a first transdermal injector means coupled to the substrate for administering a first substance to the skin to produce an appreciable breach in the surface of the skin;
a controlling means for controlling the first transdermal injection; and
second transdermal injection means coupled to the substrate for administering a medicating agent to the skin breach.

18. The transdermal drug delivery system of claim 17, further comprising a third transdermal injector which administers a protective substance to the skin breach, the controlling means controlling the second injector means and the third transdermal injector to administer the protective substance after the medicating agent.

19. A transdermal drug delivery system for providing controlled doses of a drug through the skin of a human or other animal, the transdermal drug delivery system comprising:
a thin adhesive substrate designed to adhere to skin;
a plurality of piezoelectric-driven transdermal injectors coupled to the substrate, the transdermal injectors configured to administer sequentially a plurality of different substances to the skin;
a controller which controls at least a first of the transdermal injectors to administer including a first substance to the skin to produce an appreciable breach in the surface of the skin and at least a second of the transdermal injectors to administer a medicating agent to the skin breach.

20. The transdermal drug delivery system of claim 19, wherein at least one of the transdermal injectors includes a holding chamber having one or more nozzles, and wherein the holding chamber has a plurality of actuators configured to be operated in a plurality of combinations to produce a plurality of jet velocities.

21. The transdermal drug delivery system of claim 19, wherein at least one of the piezoelectric driven transdermal injectors includes at least two injector units which separately and concurrently administer at least two components which chemically react on the skin.

* * * * *